"

US010743996B2

(12) United States Patent
Bundy

(10) Patent No.: US 10,743,996 B2
(45) Date of Patent: Aug. 18, 2020

(54) AMNION PUTTY FOR CARTILAGE REPAIR

(71) Applicant: Robert L. Bundy, The Woodlands, TX (US)

(72) Inventor: Robert L. Bundy, The Woodlands, TX (US)

( * ) Notice: Subject to any disclaimer, the term of this patent is extended or adjusted under 35 U.S.C. 154(b) by 179 days.

(21) Appl. No.: 15/935,930

(22) Filed: Mar. 26, 2018

(65) Prior Publication Data
US 2018/0271660 A1 Sep. 27, 2018

Related U.S. Application Data

(60) Provisional application No. 62/476,454, filed on Mar. 24, 2017.

(51) Int. Cl.
A61F 2/30 (2006.01)
A61L 27/36 (2006.01)
A61L 27/38 (2006.01)
A61F 2/00 (2006.01)

(52) U.S. Cl.
CPC ...... A61F 2/30756 (2013.01); A61L 27/3612 (2013.01); A61L 27/3633 (2013.01); A61L 27/3817 (2013.01); A61L 27/3852 (2013.01); A61F 2/0077 (2013.01); A61F 2002/30764 (2013.01); A61L 27/3604 (2013.01); A61L 27/3654 (2013.01); A61L 2400/06 (2013.01)

(58) Field of Classification Search
CPC .................. A61F 2/30756; A61L 27/3604
See application file for complete search history.

(56) References Cited

U.S. PATENT DOCUMENTS

| 4,394,370 | A | 7/1983 | Jefferies |
| 4,472,840 | A | 9/1984 | Jefferies |
| 5,073,373 | A | 12/1991 | O'Leary et al. |
| 5,284,655 | A | 2/1994 | Bogdansky et al. |
| 5,290,558 | A | 3/1994 | O'Leary et al. |
| 5,356,629 | A | 10/1994 | Sander et al. |
| 5,503,558 | A | 4/1996 | Clokie |
| 5,520,923 | A | 5/1996 | Tjia et al. |
| 5,702,695 | A | 12/1997 | Clokie |
| 5,707,962 | A | 1/1998 | Chen et al. |
| 5,733,868 | A | 3/1998 | Peterson et al. |
| 6,030,635 | A | 2/2000 | Gertzman et al. |
| 6,197,061 | B1 * | 3/2001 | Masuda ............ A61F 2/30756 |
| | | | 435/366 |
| 6,309,659 | B1 | 10/2001 | Clokie |
| 6,511,958 | B1 * | 1/2003 | Atkinson ............ A61F 2/30756 |
| | | | 424/422 |
| 6,623,748 | B2 | 9/2003 | Clokie |
| 7,205,337 | B2 | 4/2007 | Kay et al. |
| 7,241,813 | B2 | 7/2007 | Kay et al. |
| 7,316,801 | B2 | 1/2008 | Kercso et al. |
| 7,425,322 | B2 | 9/2008 | Cohn et al. |
| 7,553,913 | B2 | 6/2009 | Wellisz et al. |
| 7,621,963 | B2 | 11/2009 | Simon et al. |
| RE41,286 | E * | 4/2010 | Atkinson ............ A61K 9/5153 |
| | | | 424/422 |
| 7,771,741 | B2 | 8/2010 | Drapeau et al. |
| 7,785,634 | B2 | 8/2010 | Boden |
| 7,829,616 | B2 | 11/2010 | Wellisz et al. |
| 7,838,022 | B2 | 11/2010 | Drapeau et al. |
| 7,892,577 | B2 | 2/2011 | Borden |
| 8,039,016 | B2 | 10/2011 | Drapeau et al. |
| 8,124,687 | B2 | 2/2012 | Wellisz et al. |
| 8,282,953 | B2 | 10/2012 | Drapeau et al. |
| 8,394,419 | B2 | 3/2013 | Borden |
| 8,431,147 | B2 | 4/2013 | Drapeau et al. |
| 8,506,983 | B2 | 8/2013 | Mohan et al. |
| 8,840,913 | B2 | 9/2014 | McKay et al. |
| 9,056,150 | B2 | 6/2015 | Gross et al. |
| 9,132,208 | B2 | 9/2015 | Chen et al. |
| 9,138,508 | B2 | 9/2015 | Borden |
| 9,138,509 | B2 | 9/2015 | Sunwoo et al. |
| 9,308,292 | B2 | 4/2016 | Winterbottom et al. |
| 9,364,582 | B2 | 6/2016 | Drapeau et al. |
| 9,408,875 | B2 | 8/2016 | Masinaei et al. |

(Continued)

FOREIGN PATENT DOCUMENTS

| WO | 2004/071452 A2 | 8/2004 |
| WO | 2007/101171 A3 | 9/2007 |
| WO | 2007/107012 A1 | 9/2007 |

OTHER PUBLICATIONS

Ozgenel, Guzin, et al., "Effects of Human Amniotic Fluid on Cartilage Regeneration from Free Perichondrial Grafts in Rabbits", The British Association of Plastic Surgeons (2004) 57, 423-428.
Willett, Nick J., et al., "Intra-Articular Injection of Micronized Dehydrated Human Amnion/Crorion Membrane Attenuates Osteoarthritis Development", Arthritis Research & Therapy 2014, 16:R47, http://arthritis-research.com/content/16/1/R47.
Cheng, Aixin, et al., "Cartilage Repair Using Human Embryonic Stem Cell-Derived Chondroprogenitors", Stem Cells Translational Medicine 2014; 3:128701294, www.StemCellsTM.com.
Karacal, Naci, et al., "Effect of Human Amniotic Fluid on Bone Healing", Journal of Surgical Research 129, 283-297 (2005).
"Amniotic Membrane Used to Repair Human Articular Cartilage", Spanish Foundation of Science and Technology, Jun. 23, 2010, 2 pp.
"Amniotic Membrane Used to Repair Human Articular Cartilage", ScienceDaily Jun. 23, 2010, 2 pp.

(Continued)

Primary Examiner — Bruce E Snow
Assistant Examiner — Melissa A Hoban
(74) Attorney, Agent, or Firm — James A. Sheridan; Sheridan Law, LLC

(57) ABSTRACT

There are disclosed compositions for achieving reverse phase characteristics, methods of preparation thereof, and the use of amniotic tissue for cartilage repair. In an embodiment, a biocompatible articular tissue repair composition may have a therapeutic material and a carrier configured for achieving reverse phase characteristics, and methods for using the composition. In various embodiments, the therapeutic material may be amniotic tissue. In various embodiments, the carrier may be a poloxamer such as poloxamer 407. Other embodiments are also disclosed.

13 Claims, No Drawings

(56) References Cited

U.S. PATENT DOCUMENTS

| | | |
|---|---|---|
| 9,463,264 B2 | 10/2016 | Ortiz et al. |
| 9,486,483 B2 | 11/2016 | Bhat et al. |
| 9,539,286 B2 | 1/2017 | Bhat et al. |
| 9,579,421 B2 | 2/2017 | Bhat et al. |
| 9,616,150 B2 | 4/2017 | Levy et al. |
| 9,730,982 B2 | 8/2017 | McKay et al. |
| 9,919,074 B2 | 3/2018 | Wellisz et al. |
| 2002/0123091 A1* | 9/2002 | Gurney .............. C07K 14/4705 435/69.1 |
| 2002/0168381 A1* | 11/2002 | Shimura ................... A61F 2/28 424/193.1 |
| 2003/0175322 A1 | 9/2003 | Kay et al. |
| 2003/0175410 A1* | 9/2003 | Campbell ............... A61L 27/38 427/2.24 |
| 2004/0022858 A1 | 2/2004 | Clokie |
| 2004/0076677 A1 | 4/2004 | Kay et al. |
| 2004/0181047 A1* | 9/2004 | Rosen ................... C07K 14/47 536/23.2 |
| 2004/0248156 A1* | 12/2004 | Hu ........................ C07K 14/47 435/6.11 |
| 2005/0020506 A1 | 1/2005 | Drapeau et al. |
| 2005/0165128 A1 | 7/2005 | Cohn et al. |
| 2006/0100370 A1 | 5/2006 | Wellisz et al. |
| 2006/0110357 A1 | 5/2006 | Materna et al. |
| 2006/0140904 A1 | 6/2006 | Wellisz et al. |
| 2006/0233849 A1 | 10/2006 | Simon et al. |
| 2006/0233851 A1 | 10/2006 | Simon et al. |
| 2007/0202190 A1 | 8/2007 | Borden |
| 2007/0202191 A1 | 8/2007 | Borden |
| 2007/0254041 A1 | 11/2007 | Drapeau et al. |
| 2008/0050377 A1* | 2/2008 | Ackerly ................. C07K 16/22 424/138.1 |
| 2008/0063684 A1 | 3/2008 | Winterbottom et al. |
| 2009/0074871 A1 | 3/2009 | Sunwoo et al. |
| 2009/0142385 A1 | 6/2009 | Gross et al. |
| 2009/0143830 A1 | 6/2009 | Bourgeois et al. |
| 2009/0246244 A1 | 10/2009 | McKay et al. |
| 2009/0298761 A1* | 12/2009 | Engelman .......... A61K 38/1875 514/1.1 |
| 2010/0036503 A1 | 2/2010 | Chen et al. |
| 2010/0209470 A1 | 8/2010 | Mohan et al. |
| 2010/0209474 A1 | 8/2010 | Drapeau et al. |
| 2010/0254900 A1* | 10/2010 | Campbell ............... A61L 27/18 424/1.65 |
| 2010/0255115 A1 | 10/2010 | Mohan et al. |
| 2011/0002915 A1 | 1/2011 | Wellisz et al. |
| 2011/0002974 A1 | 1/2011 | Wellisz et al. |
| 2011/0081311 A1* | 4/2011 | Pavlakis ............... A61K 9/0019 424/85.2 |
| 2011/0104299 A1 | 5/2011 | Borden |
| 2014/0030338 A1 | 1/2014 | Royle et al. |
| 2015/0216912 A1* | 8/2015 | Koob ..................... A61K 35/50 424/93.7 |
| 2015/0320833 A1* | 11/2015 | Stice ....................... A61L 27/18 424/489 |
| 2016/0193385 A1* | 7/2016 | Tian ............................ C08J 9/26 424/422 |
| 2017/0361534 A1* | 12/2017 | Fernandez-Nieves ........ B33Y 70/00 |
| 2018/0100139 A1* | 4/2018 | Ryzhuk ................... A61K 35/50 |
| 2018/0126036 A1* | 5/2018 | Early ....................... A61K 35/50 |
| 2018/0361026 A1* | 12/2018 | Qin ........................ A61K 35/50 |

OTHER PUBLICATIONS

Fortier, Lisa A., et al., "The Role of Growth Factors in Cartilage Repair", Clin Orthop Relat Res Oct. 2011; 469(10): 2706-2715.

Anderson, John Joseph, et al., "Human Amniotic Allograft in Use on Talar Dome Lesions: A Prospective Report of 37 Patients", Stem Cell Discovery, 2014, 4, 55-60. http://www.scirp.org/journal/scd.

* cited by examiner

AMNION PUTTY FOR CARTILAGE REPAIR

REFERENCE TO PENDING PRIOR PATENT APPLICATION

This application claims the benefit under 35 U.S.C. 119 (e) of U.S. Provisional Patent Application No. 62/476,454, filed Mar. 24, 2017 by Robert L. Bundy for "AMNION PUTTY FOR CARTILAGE REPAIR," which patent application is hereby incorporated herein by reference.

BACKGROUND

Chondral defects and osteoarthritis in all articulating joints in the human body continue to present major challenges for the orthopedic surgeon because of the limited healing potential of articular cartilage. Several different therapeutic methods are currently being used to repair damaged cartilage. Current methods include, but are not necessarily limited to, implantation of chondrocytes, whether they be juvenile or adult, via a patch or putty; fresh allograft chondral plugs; surgical microfracture to stimulate cartilage growth; and amniotic fluid injections. Generally, all of these fall short in regenerating hyaline cartilage.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a biocompatible articular cartilage tissue repair composition, comprising amniotic tissue, and a reverse phase mixture of poloxamer and water, wherein the composition exhibits reverse phase behavior and is non-liquid at ambient and body temperatures.

In one embodiment, the poloxamer is poloxamer 407.

In an embodiment, the mixture of poloxamer and water is 25 percent weight poloxamer and 75 percent weight water.

In another embodiment, the composition is 30 percent weight amniotic tissue and 70 percent weight poloxamer and water.

In another embodiment, wherein the composition is 50 percent weight amniotic tissue and 50 percent weight poloxamer and water.

In yet another embodiment, there is provided a method to repair cartilage tissue, the method comprising providing a biocompatible cartilage repair composition, comprising amniotic tissue, and a reverse phase mixture of poloxamer and water, wherein the composition exhibits reverse phase behavior and is non-liquid at ambient and body temperatures; and placing the composition in a cartilage defect of a mammal.

In one embodiment, the method includes the step of placing the composition in the cartilage defect of a mammal includes placing the composition in a liquid state at a given temperature below the ambient and body temperatures.

In an embodiment, the method includes the step of placing the composition in the cartilage defect of a mammal includes allowing the composition to transition to a non-liquid at the ambient and body temperatures so as to resist displacement from the cartilage defect.

In still another embodiment, there is disclosed a biocompatible articular cartilage tissue repair composition, comprising a reverse phase mixture of poloxamer and amniotic fluid; wherein the composition exhibits reverse phase behavior and is non-liquid at ambient and body temperatures.

Other embodiments are also disclosed.

Additional objects, advantages and novel features of the technology will be set forth in part in the description which follows, and in part will become more apparent to those skilled in the art upon examination of the following, or may be learned from practice of the technology.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Through literature research, it is documented that the anabolic and anticatabolic effects of a variety of growth factors have demonstrated potential in both in vitro and animal studies of cartilage injury and repair. Key chondrogenic factors are:

TGF-β1,3: Promotes chondrogenic differentiation and regulates type II collagen expression.

BMP2,4,7: Induces chondrogenesis of MSC's and stimulates ECM production by chondrocytes.

bFGF: Stimulates proliferation of chondrocytes.

IGF-1: Induces ECM synthesis.

Members of the transforming growth factor-β superfamily, fibroblast growth factor family and insulin-like growth factor-I have all been investigated as possible treatment augments in the management of chondral injuries and early osteoarthritis. Also, proteomic studies of amniotic tissue show that the placenta has substantial number of growth factors such as, but not limited to, bFGF, BMP-2, EGF, PDGF-AA, PDGF-BB, TGF-β1, FGF, VEGF, CTGF, and IGF.

Amniotic tissue has benefits as an implantable material. Amniotic tissue contains substantial number of growth factors needed in cartilage regeneration. The challenge is keeping the amniotic tissue in place while its therapeutic value can take hold in an articulating joint filled with synovial fluid.

Various embodiments herein provide an articulating cartilage repair composition which stimulates the body's own mesenchymal stem cells to differentiate into chondrocytes thus repairing the cartilage defect. In embodiments, this may be a formulation that is easily to apply to a cartilage defect in either an open or endoscopic procedure, and which remains at the site once placed.

In an embodiment, there is disclosed a biocompatible composition to facilitate repair of articulating cartilage. The composition may include amniotic tissue, and, a carrier comprising a means of achieving reverse phase thermodynamic characteristics when mixed or otherwise combined with amniotic tissue. The composition is configured to resist displacement once implanted inasmuch as the composition is substantially liquid at 0° C. (i.e., at lower temperature than ambient or body temperature) and substantially more viscous at 35° C. (i.e., at higher temperature than liquid phase; ambient or body temperatures.)

A poloxamer, such as poloxamer 407, may be used to achieve reverse phase characteristics in a dispersed configuration in a biocompatible solvent such as sterile water. Preferably the total carrier comprises a carrier of 25 weight percent of the poloxamer 407 dispersed in 75 weight percent of a biocompatible solvent. To vary the consistency of the composition, the weight percentage of amniotic tissue can be varied relative to the weight percentage of the carrier. For example, a paste-like form of the composition comprises 50 weight percent of amniotic tissue and 50 weight percent of a carrier. A gel-like embodiment of the composition comprises 30 weight percent of amniotic tissue and 70 weight percent of a carrier. Amniotic tissue may be pre-treated in a number of ways prior to the addition of the carrier. Pretreatment may include various amounts of cutting, blending, chopping or mixing the amniotic tissue either alone or with the carrier material. The amniotic tissue may be treated to remove or add constituents either before or after addition of the carrier.

Also disclosed is a method to the development of cartilage tissue, the method includes providing a biocompatible cartilage repair composition. In an embodiment, the composition includes amniotic tissue, a carrier of a reverse phase mixture of poloxamer and water, wherein the composition exhibits reverse phase behavior when the carrier is mixed with the amniotic tissue and is non-liquid at ambient and body temperatures. The composition resists displacement at body temperatures. The method includes placing the composition in a cartilage defect of a mammal. A prosthetic object can also be placed in the cartilage defect. The method can also comprise coating a portion of the prosthetic object with the biocompatible composition, and in this embodiment the step of placing the composition and the step of placing a prosthetic object can be contemporaneous.

MODES FOR CARRYING OUT VARIOUS EMBODIMENTS

Definitions

By "reverse phase" or "reverse thermal behavior" is intended a material that exhibits a physical of becoming more viscous or solidifies upon implantation in a cartilage defect of a mammal.

As used herein, "ambient temperature" is 25° C., plus or minus 5° C.

As used herein, "body temperature" is 37° C. plus or minus 5° C.

As used herein, a "cartilage defect" is an articulating cartilage of a mammal which comprises some viable cartilage tissue. The defect can be congenital, caused by trauma, or caused by disease.

Examples

In an embodiment, the composition may be a flowable liquid when applied to cartilage defect, whereupon the composition becomes increasingly solidified or viscous as it warms from an ambient temperature (or from below ambient temperature) to the body temperature of the mammal. Upon being warmed to body temperature, the composition may be solid or highly viscous and resistant to displacement due to synovial fluid. The reverse phase compositions in accordance with the present disclosure are significantly different from cartilage repair materials in the prior art and do not function in the same way.

The composition may include a therapeutic material for treating cartilage defects and a carrier. The therapeutic material can be a material that contains substantial number of growth factors needed in cartilage regeneration. The carrier achieves reverse phase characteristics when mixed with the therapeutic material.

The therapeutic material can be a material, such as amniotic membrane, amniotic liquid, umbilical cord, or a combination thereof, that has a substantial number of growth factors that are instrumental in cartilage regeneration. The therapeutic material may be provided in various sized tissues, including substantially whole tissues to morcellated tissues into small pieces, liquid or a combination of solid tissue pieces with amniotic liquid components. As may be appreciated by one of ordinary skill in the art, the therapeutic material can comprise combinations of various therapeutic materials.

In one embodiment, the biocompatible carrier of the composition is a material that confers reverse phase thermodynamic properties on the composition. The use of PLURONIC® F127 as a component of an osteointegration promoting composition is set forth in U.S. Pat. No. 5,503,558, issued Apr. 2, 1996 to the inventor herein, Cameron M. L. Clokie; and in PCT International Publication No. WO 95/13099. In a presently preferred embodiment, the carrier comprises a polymer marketed by BASF (Parsipanny, N.J.) as PLURONIC® F127. PLURONIC® F127 is a poly(oxyalkylene) block copolymer; more specifically, a poly(oxyethylene)-poly(oxypropylene)-poly(oxyethylene) triblock copolymer; it is a member of a class of compounds called poloxamers. (Schmolka, "A Review of Block Polymer Surfactants" *J. Am. Oil Chemists Soc.* 54:110-116 (1977)). Several members of the poloxamer family exhibit reverse phase thermodynamic characteristics. PLURONIC® F127 is also known by the name "poloxamer 407." (Schmolka, "A Comparison of Block Polymer Surfactant Gels" *J. Am. Oil Chemist Soc.* 68:206-209 (1991)). PLURONIC® F127 has an average molecular weight of approximately 12,500. (Schmolka, "A Comparison of Block Polymer Surfactant Gels" *J. Am. Oil Chemist Soc.* 68:206-209 (1991)) The structure of the PLURONIC® F127 polymer is depicted as follows:

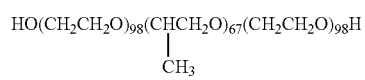

In various embodiments of a composition of the present disclosure, the carrier is a liquid diluted in a solvent or is a solid dispersed in a solvent. In one embodiment, PLURONIC® F127 is dispersed in a solvent such as sterile water. The PLURONIC® F127 carrier is vastly different in size, molecular weight, and chemical structure than carriers in the art. The carrier is also substantially different in terms of its functional properties than any carrier of a cartilage repair material in the art.

The composition has a unique physical property for cartilage repair of being flowable at refrigerated temperatures which will become viscous at body temperature and will also be resistant to displacement after implantation. The unique reverse phase thermodynamic properties of the composition for cartilage repair allow various embodiments to function in a substantially different and advantageous manner relative to other flowable cartilage repair products. When applied to a cartilage defect, the reverse phase property of the preferred carrier provides support characteristics for the composition which are substantially different than the characteristics of standard carriers. This is because the composition is flowable at room temperature and can be applied to a cartilage defect, but becomes increasingly viscous and solidified once warmed at the defect site. The solidification of the composition of the present disclosure achieves several beneficial effects. When solidified, the composition does not flow away from the defect site, and the solidified product immediately augments and facilitates therapeutic support at the site. Also, since the amniotic composition of the present disclosure is initially liquid, it readily fills the cartilage defect, then becomes solidified and achieves enhanced cartilage regeneration.

In another embodiment, a biocompatible articular cartilage tissue repair composition may include a reverse phase mixture of poloxamer and amniotic fluid. Water may or may not be a necessary component. The composition is configured to exhibit reverse phase behavior and is non-liquid at ambient and body temperatures. In an embodiment, the poloxamer is poloxamer 407. The mixture of poloxamer and amniotic fluid may be a provided in various ratios. In one embodiment, the mixture is 25 percent weight poloxamer and 75 percent weight amniotic fluid. In an embodiment, the composition is 30 percent weight amniotic fluid and 70 percent weight poloxamer. In another embodiment, the composition is 50 percent weight amniotic fluid and 50 percent weight poloxamer.

For example, one carrier may be PLURONIC® F127 as the carrier in the composition of an embodiment of the composition. PLURONIC® F127 (when dispersed in an appropriate amount of sterile water) has the unique property of being a liquid at refrigerated temperature and increasingly solidified, then solid at elevated temperature, absent the effects of evaporation and concomitant loss of water. This property is called "reverse phase" or "reverse thermal behavior" because it is the exact opposite of the thermodynamic properties exhibited by standard carriers.

It is believed that the reverse phase property is due, at least in part, to the fact that PLURONIC® F127 is composed of discrete blocks of both hydrophilic (i.e., oxyethylene) and hydrophobic (i.e., oxypropylene) subunits. (See e.g., Schmolka, "A Comparison of Block Polymer Surfactant Gels" *J. Am. Oil Chemist Soc.* 68:206-209 (1991)).

In contrast, standard carriers, as well as all liquids, manifest the typical physical property of becoming increasingly flowable upon addition of thermal energy, such as occurs when the liquid is heated to body temperature. However, the preferred carrier in a composition of the present invention becomes less flowable as energy is added to it either by heating or by shaking.

The unique reverse phase thermodynamic properties of the composition of the various embodiments herein allow the product to function in a substantially different, and preferred manner relative to other cartilage repair products. When applied to a cartilage defect site, the reverse phase property of the carrier provides support characteristics for the composition which are substantially different than the characteristics of standard carriers. Enhanced support is provided by the composition of various embodiments. In various embodiments, the PLURONIC® F127 carrier of the composition of one embodiment helps to provide support characteristics which are unlike those of any standard carrier. This is because the composition is flowable at refrigerated temperature and can thus readily be applied to a cartilage defect site, but it becomes increasingly viscous and solidified once it is warmed at the site. The solidification of the composition of various embodiments achieves several beneficial effects. When solidified, the composition does not flow away from the defect site, and the solidified product immediately augments and facilitates structural support at the defect. Also, since the cartilage regenerative composition is initially liquid, it readily fills a defect, then becomes solidified and achieves enhanced cartilage regeneration. Moreover, with various compositions comprising a sterile aqueous colloidal suspension of PLURONIC® F127 as carrier and amniotic tissue, the carrier will resorb or dissolve after about three days, leaving the amniotic tissue at the cartilage defect site. It is believed to be advantageous that the carrier disperses as this then allows for enhanced ingrowth of connective or vascular tissues.

In a composition of various embodiments, the weight percentages of the therapeutic material and the carrier can each be varied. For example, the weight percent of the therapeutic material can vary between about 20 to 80 weight percent of the composition, and the weight percent of the carrier can vary between about 20 to 80 weight percent of the composition. Furthermore one or more additional components can be present in a composition of various embodiments, such as antibiotics, analgesic, anti-inflammatory agents, or agents to promote development of connective or circulatory system tissues.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A biocompatible articular cartilage tissue repair composition, comprising:
    components of amniotic tissue, and the components of the amniotic tissue including growth factors configured to regenerate cartilage at a cartilage defect site in an articulating joint containing synovial fluid; and
    a reverse phase mixture of poloxamer and a liquid, the reverse phase mixture configured as a carrier of the amniotic tissue, and the carrier configured to resorb after a first period of time at the cartilage defect site while leaving the amniotic tissue at the cartilage defect site to allow ingrowth of the amniotic tissue into the cartilage defect site;
    wherein the composition exhibits reverse phase behavior, wherein the composition is non-liquid at ambient and body temperatures, and wherein the composition supports the amniotic tissue with the carrier at the cartilage defect site for the first period of time for the carrier to resorb, and wherein the composition further supports the amniotic tissue with ingrowth during and subsequent to the first period of time so as to maintain the growth factors configured to regenerate cartilage at the cartilage defect site for a second period of time, the second period of time being longer than the first period of time, as the amniotic tissue is kept in place within the articulating joint containing synovial fluid; and
    wherein the components of the amniotic tissue include at least one of cut amniotic tissue, blended amniotic tissue, chopped amniotic tissue, and mixed amniotic tissue.

2. The composition of claim 1, wherein the poloxamer is poloxamer 407.

3. The composition of claim 1, wherein the amniotic tissue is xenogeneic, allogeneic or autogenic.

4. The composition of claim 3, wherein xenogenic tissue from a porcine or bovine source is the amniotic tissue.

5. The composition of claim 1, wherein the liquid is water.

6. The composition of claim 5, wherein the mixture of poloxamer and water is 25 percent weight poloxamer and 75 percent weight water.

7. The composition of claim 5, wherein the composition is 30 percent weight amniotic tissue and 70 percent weight poloxamer and water.

8. The composition of claim 5, wherein the composition is 50 percent weight amniotic tissue and 50 percent weight poloxamer and water.

9. A biocompatible articular cartilage tissue repair composition, comprising:
   therapeutic material for treating a cartilage defect site, the therapeutic material including components of amniotic tissue; and
   a reverse phase mixture of poloxamer and a liquid, the reverse phase mixture configured as a carrier of the components of the amniotic tissue, and the carrier configured to resorb after a first period of time at the cartilage defect site while leaving the components of the amniotic tissue at the cartilage defect site to allow ingrowth of the components the amniotic tissue into the cartilage defect site;
   wherein the composition exhibits reverse phase behavior and is non-liquid at ambient and body temperatures, wherein the composition is non-liquid at ambient and body temperatures, and wherein the composition supports the components of the amniotic tissue with the carrier at the cartilage defect site for the first period of time for the carrier to resorb, and wherein the composition further supports the components of the amniotic tissue with ingrowth during and subsequent to the first period of time so as to regenerate cartilage at the cartilage defect site for a second period of time, the second period of time being longer than the first period of time, as the components of the amniotic tissue are kept in place within an articulating joint containing synovial fluid and
   wherein the components of the amniotic tissue include at least one of cut amniotic tissue, blended amniotic tissue, chopped amniotic tissue, and mixed amniotic tissue.

10. The composition of claim 9, wherein the therapeutic material for treating the cartilage defect contains a number of growth factors for cartilage regeneration.

11. The composition of claim 9, wherein the liquid is water.

12. A biocompatible articular cartilage tissue repair composition, comprising:
   components of tissue, and the components of tissue including growth factors configured to regenerate cartilage at a cartilage defect site in an articulating joint containing synovial fluid; and
   a reverse phase mixture of poloxamer and a liquid, the reverse phase mixture configured as a carrier of the tissue, and the carrier configured to resorb after a first period of time at the cartilage defect site while leaving the components of tissue at the cartilage defect site to allow ingrowth of the components of tissue into the cartilage defect site;
   wherein the composition exhibits reverse phase, wherein the composition is non-liquid at ambient and body temperatures, and wherein the composition supports the components of tissue with the carrier at the cartilage defect site for the first period of time for the carrier to resorb, and wherein the composition further supports the components of tissue with ingrowth during and subsequent to the first period of time so as to maintain the growth factors configured to regenerate cartilage at the cartilage defect site for a second period of time, the second period of time being longer than the first period of time, as the components of tissue is kept in place within the articulating joint containing synovial fluid;
   wherein the components of the tissue include at least one of cut amniotic tissue, blended amniotic tissue, chopped amniotic tissue, and mixed amniotic tissue.

13. The composition of claim 12, wherein the poloxamer is poloxamer 407.

* * * * *